United States Patent
Fioravanti

(10) Patent No.: US 8,818,821 B2
(45) Date of Patent: Aug. 26, 2014

(54) DIGITAL ASSISTANT APPLIANCE FOR ASSISTING AN OPERATOR IN THE MANUAL PREPARATION OF A LIQUID PHARMACEUTICAL COMPOSITION IN A MEDICAL INSTRUMENT FOR ADMINISTERING THE COMPOSITION TO A PATIENT, AND CORRESPONDING OPERATING METHOD

(75) Inventor: Fabio Fioravanti, Trieste (IT)

(73) Assignee: Medarchiver S.R.L., Bolzano (IT)

( * ) Notice: Subject to any disclaimer, the term of this patent is extended or adjusted under 35 U.S.C. 154(b) by 0 days.

(21) Appl. No.: 12/829,559

(22) Filed: Jul. 2, 2010

(65) Prior Publication Data

US 2011/0191121 A1    Aug. 4, 2011

(30) Foreign Application Priority Data

Jan. 29, 2010  (EP) .................................... 10425018

(51) Int. Cl.
  *G06F 19/00*    (2011.01)
(52) U.S. Cl.
  USPC ................................................ 705/3; 705/2
(58) Field of Classification Search
  USPC ............................................................ 705/3
  See application file for complete search history.

(56) References Cited

U.S. PATENT DOCUMENTS

| 5,597,995 | A | 1/1997 | Williams et al. |
| 7,930,066 | B2 * | 4/2011 | Eliuk et al. .................... 700/245 |
| 2005/0279419 | A1 | 12/2005 | Tribble et al. |
| 2007/0041871 | A1 * | 2/2007 | Lecrone ......................... 422/61 |
| 2008/0125897 | A1 * | 5/2008 | DiGianfilippo et al. ...... 700/110 |
| 2009/0154764 | A1 | 6/2009 | Khan et al. |

OTHER PUBLICATIONS

Extended European Search Report from European Application No. 10168232.6 dated Oct. 8, 2013.

* cited by examiner

*Primary Examiner* — Hiep V Nguyen
(74) *Attorney, Agent, or Firm* — Dorsey & Whitney LLP

(57) ABSTRACT

Digital assistant appliance for assisting an operator in the manual preparation of a liquid pharmaceutical composition comprising: a memory device containing, for each active principle of the liquid pharmaceutical composition: one or more first sample images of vials containing the active principle, and one or more second sample images of syringes that can be used for transferring the active principle from the vials to the medical instrument; an artificial viewing system designed to acquire: a vial image of a vial chosen by the operator and/or a syringe image of a syringe chosen by the operator; and an electronic processing system configured in such a way as to compare the vial image with each of the first sample images for determining whether the vial chosen by the operator is incorrect, and/or compare the syringe image with each of the second sample images for determining whether the syringe chosen by the operator is incorrect, and warn the operator of an error condition in the preparation step when the vial or the syringe chosen by the operator is incorrect.

18 Claims, 12 Drawing Sheets

Fig. 10

DIGITAL ASSISTANT APPLIANCE FOR ASSISTING AN OPERATOR IN THE MANUAL PREPARATION OF A LIQUID PHARMACEUTICAL COMPOSITION IN A MEDICAL INSTRUMENT FOR ADMINISTERING THE COMPOSITION TO A PATIENT, AND CORRESPONDING OPERATING METHOD

The present invention relates to a digital assistant appliance configured to assist an operator in the manual preparation of a liquid pharmaceutical composition in a medical instrument for administering said pharmaceutical composition to a patient, as well as the corresponding operating method.

In particular, the present invention relates to a digital assistant appliance configured to assist an operator in selecting and dosing one or more drugs, referred to hereinafter by the term "active principles", in the course of preparation of a liquid pharmaceutical composition to be injected via intravenous route to a patient, through an medical instrument for administering the liquid pharmaceutical composition itself, such as for example a syringe, or a intravenous drip, or an infusion sac, or an elastomeric pump or any other similar medical instrument, to which the following description will refer purely by way of example.

BACKGROUND OF THE INVENTION

As is known, the preparation of liquid pharmaceutical compositions to be administered to patients is carried out typically by medical or pharmaceutical operators in appropriate sterilized/decontaminated rooms using doses, i.e., preset amounts/weights of one or more active principles prescribed in a medical prescription.

In particular, the operator prepares the liquid pharmaceutical composition by carrying out the following operations: selecting and taking from a store the vials containing the active principles present in the medical prescription; drawing from the vials, using sterile syringes, the preset doses of active principles; and fitting each syringe to the administration instrument to introduce therein the dose of active principle drawn in.

Since it is performed in a completely manual way, the preparation of the liquid pharmaceutical composition described above may be subject to accidental errors, i.e., ones deriving from incorrect aspiration/dosage of the active principles in the syringes by the operator, this latter condition possibly evidently determining pharmaceutical compositions that are potentially harmful/dangerous for the patient.

In order to reduce the aforesaid risks of error, there has been devised digital assistant appliance for assisting the operator in the different steps of manual preparation of the pharmacological composition, which basically comprises: a user interface, through which the operator imparts selection commands of a pre-stored medical prescription and which displays to the operator himself, step by step, messages indicating the operations to be performed; a gravimetric control device for measuring the weight of the vials containing the active principles and the sterile syringes used for transfer of the active principle; and an electronic processing unit, which, on the basis of the weights of the vials and of the syringes, measured before and after the transfer of the active principle from the vials to the syringes, calculates the effective dose of active principle drawn in/dosed by the operator to point out any possible discordance between the dose of active principle effectively drawn in and the dose prescribed in the medical prescription.

The digital assistant appliance of the type described above presents a series of technical drawbacks.

In the first place, the weighing carried out by the gravimetric control device can be affected by errors caused by a modification of the configuration of the vial and/or of the syringe in the course of the weighing operations. It may happen in fact that, during preparation, the operator without realizing applies/removes the lid on/from the vial and/or the needle on/from the syringe and/or the protective cap of the needle on/from the syringe itself and/or a spike, thus modifying the weight measurement conditions, and consequently causing an incorrect calculation of the effective dose of active principle drawn into the syringe.

In the second place, the digital assistant appliance of the type described above considers implicitly correct the operation of selection of the vial containing the active principle by the operator and consequently is not able to detect conditions of selection of vials containing incorrect active principles.

Furthermore, the digital assistant appliance of the type described above presents the technical drawbacks of forcing the operator to choose for each active principle a preset vial and a preset syringe, this latter condition possibly preventing preparation of a liquid pharmaceutical composition when, for example, there occurs the absence of the vial and/or of the syringe envisaged in the procedure implemented by the equipment itself.

SUMMARY OF THE INVENTION

The aim of the present invention is consequently to provide digital assistant appliance for assisting an operator in the manual preparation of a liquid pharmaceutical composition in an instrument for administering said composition to a patient that is able to detect a modification of the external configuration of the vial/syringe during the operations of weighing, is able to signal in due time the use of a vial containing an incorrect active principle, and do not force the operator to select a single type of vial/syringe for transferring a preset dose of active principle.

According to the present invention, there is thus provided digital assistant appliance for assisting an operator in the manual preparation of a liquid pharmaceutical composition in an instrument for administering said composition to a patient, as claimed in the attached claims.

According to the present invention, it is also provided a method for operating the digital assistant appliance configured to assist an operator in the manual preparation of a liquid pharmaceutical composition in an instrument for administering said composition to a patient as claimed in the attached claims.

Finally, according to the present invention, a software program is provided as claimed in the attached claims.

BRIEF DESCRIPTION OF THE DRAWINGS

The present invention will now be described with reference to the attached figures, which illustrate schematically a non-limiting example of embodiment thereof.

Figure 10:
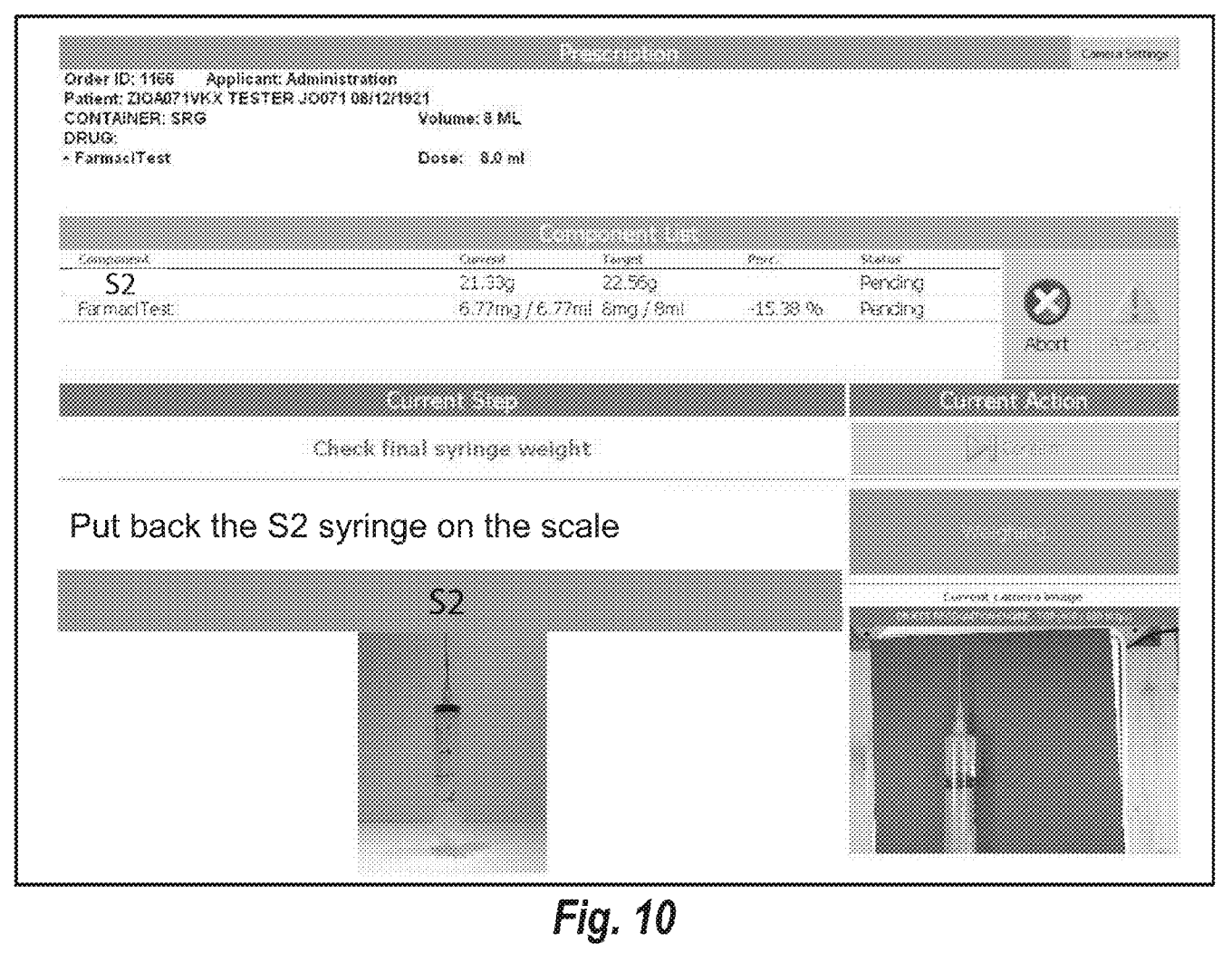

FIGS. 3 to 10 show as many graphic interfaces displayed by the digital assistant appliance illustrated in FIG. 1 during preparation of the liquid pharmaceutical composition.

DETAILED DESCRIPTION OF THE INVENTION

Figure 1:
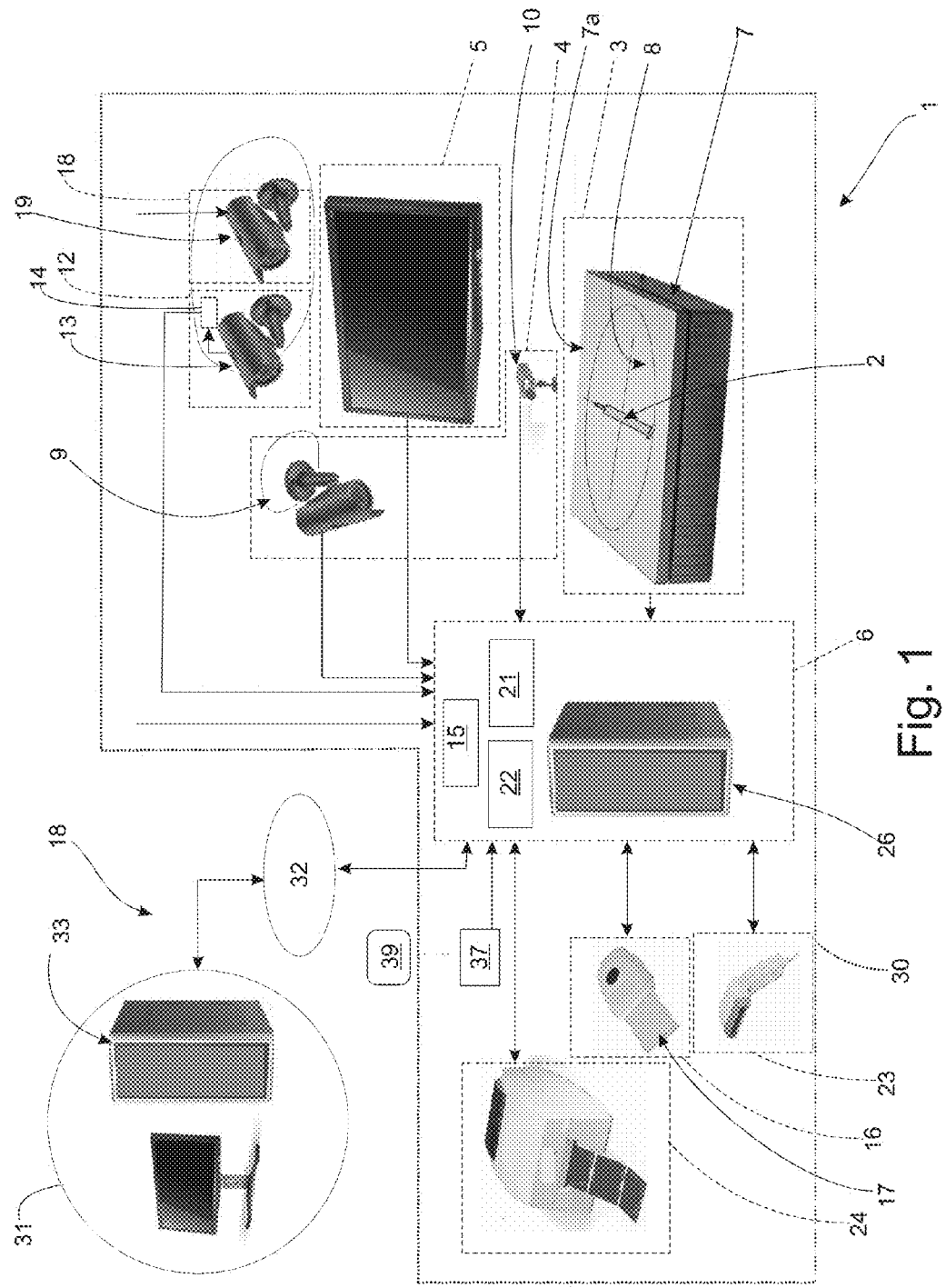
FIG. 1 is a schematic view of a digital assistant appliance for assisting an operator in the manual preparation of a liquid pharmaceutical composition in an instrument for administering said pharmaceutical composition to a patient, provided according to teachings of the present invention.

With reference to FIG. 1, designated as a whole by the reference number 1 is digital assistant appliance configured for assisting an operator in the manual preparation of a liquid pharmaceutical composition to be administered to a patient via an instrument for containment and/or administration of said liquid pharmaceutical composition to a patient.

In particular, the instrument for containment and/or administration of the liquid pharmaceutical composition, referred to hereinafter as medical instrument 2 may comprise, for example, a syringe, or an intravenous drip, or an infusion sac, or an elastomeric pump or any other type of similar medical device used typically for injecting a liquid pharmaceutical composition into a patient.

The digital assistant appliance 1 is designed to be set in a workstation 30, in which the operator executes the preparation of the liquid pharmaceutical composition, and which comprises: a gravimetric control system 3; an artificial viewing system 4; a user-interface system 5; and a processing system 6, configured to implement a method for assisting an operator in the manual preparation of a liquid pharmaceutical composition that can be administered to a patient (described in detail hereinafter).

In particular, in the example illustrated in FIG. 1, the gravimetric control system 3 comprises an electronic precision balance 7 provided with a scale 8 set on a horizontal surface, rested on which are, during preparation of the composition, a vial and/or a syringe to be weighed.

As regards the artificial viewing system 4, it comprises at least one top photographic camera or videocamera 9, which is set above the scale 8 of the electronic balance 7 in such a way as to acquire images containing the view from above of the vial or of the syringe set on the scale 8; and at least one front photographic camera or videocamera 10, which is set facing a preset side 7a of the scale 7 to acquire the image of the front side of the vial or of the syringe, facing precisely the preset side 7a.

As regards the user-interface system 5, it comprises a display device, for example a screen or display, a user control device, for example a keyboard, and preferably a device for reproducing voice messages. In the example illustrated in FIG. 1, the display device, the user control device, and the device for reproducing voice messages are conveniently integrated in a single device corresponding to a touch screen.

The digital assistance equipment 1 is moreover provided with a user-authentication system 12 comprising: a biometric-recognition photographic camera or videocamera 13 designed to acquire the images of the operator, for example the facial image or image of parts of the face, such as for example the eyes; and an access module or device 14, which processes the operator image, carries out a comparison between the latter and a corresponding operator sample image contained in a memory device 15 of the digital assistant appliance 1, and authorizes or denies access to the operator himself on the basis of the outcome of said comparison.

In particular, the access device 14 can be configured to carry out the aforesaid comparison between the images by implementing a pattern-matching recognition algorithm, which will not be described in detail in so far as it is known.

The user-authentication system 12 moreover preferably, but not necessarily, comprises a smartcard-reading device 16, which is able to read operator data contained in an operator smartcard 17 and uniquely identifies an operator.

The digital assistant appliance 1 moreover preferably, but not necessarily, comprises an RFID (Radio Frequency IDentification) data-reading system 35, comprising one or more tags or transponders 36 and a transponder-reader apparatus 37, which is able to read data contained in the transponder 36. In the case in point, each transponder 37 is provided with an internal memory containing the data that uniquely identify a corresponding operator.

In use, the step of authentication of the operator envisages reading operator data contained in the transponder 37 by the transponder-reader apparatus 37.

The access device 14 can be configured to process the operator data provided by the smartcard-reading device 16 and authorizes or denies access to the operator on the basis of the outcome of the processing.

In particular, the operator data contained in the operator smartcard 17 could comprises a digital signature and/or a recognition PIN (Personal Identification Number) or any other similar data that enables unique identification of the operator.

The digital assistant appliance 1 preferably but not necessarily further comprises a monitoring system 18, which is configured in such a way as to enable viewing of the operations carried out by the operator in the station 30 from a remote-surveillance station 31.

The monitoring system 18 comprises a field photographic camera or videocamera 19 set in the workstation 30 to acquire the images regarding the different steps of preparation of the liquid pharmaceutical composition by the operator so as to produce a video film; a communication module 21 connected to the remote-surveillance station 31 through a data-communication network 32 to transmit the video film acquired to the remote-surveillance station 31; and a processing module 22 that controls the video field camera 19, issues a command for storage of the video film in the memory device 15, and issues a command for transmission of the video film itself in the data-communication network 32 through the communication module 21.

The remote-surveillance station 31 can comprise a computer 33 connected to the data-communication network 32 for receiving and storing the film, and is configured to enable conveniently remote monitoring of the workstation 30, and/or viewing of the film regarding preparation of a given liquid pharmaceutical composition; and/or monitoring in real time of the state of advance of the preparation of said composition.

The digital assistant appliance 1 moreover preferably but not necessarily comprises: a barcode-reader device 23; and a printing device 24 designed to print labels containing data regarding the liquid pharmaceutical composition for the operator and regarding the preparation.

As regards the processing system 6, it comprises the memory device 15 described above, which, in addition to containing the data for identification of the operator, comprises a database designed to contain the medical prescriptions associated to the pharmaceutical compositions to be administered to the patients.

In particular, each medical prescription associated uniquely to a liquid pharmaceutical composition of a patient contains: the data regarding the active principle or principles to be used for the preparation of the liquid pharmaceutical composition; the dose, i.e., the weight or amount of each active principle; the different types of syringes that can be used during preparation, where each type of syringe is characterized by a preset external structure/shape and by its containing capacity; the different types of vials containing the same active principle, where each type of vial can be characterized by the external shape, and/or by a containing capacity and/or by the data contained on an identification label affixed to the vial. In the case in point, the data contained on the label comprise, for example, the manufacturer of the active principle and preferably but not necessarily a barcode.

The memory device 15 moreover contains, for each type of syringe, a syringe sample image and, for each type of vial, a vial sample image.

The memory device 15 can moreover contain, for each type of syringe a corresponding sample image of a syringe-spike configuration, which represents the image of the syringe itself coupled to a preset spike, and for each type of vial a corresponding sample image of a vial-spike configuration, which represents as a whole an image of the vial coupled to a preset spike.

From what has been described above, it should be noted that in what follows, by the term "spike" will be understood a perforating device, which, since it is known, will not be described any further except to point out that it is structured in such a way that it can be fitted to a vial through an operation that envisages perforation of the vial, and/or to a syringe through a connector.

The processing system 6 further comprises a processing device 26, which is configured to implement a method for assisting an operator in the manual preparation of a liquid pharmaceutical composition.

The method comprises a series of operations/instructions coded in a software program that can be stored in the memory device 15 and that can be loaded into the processing device 26 in a such way that the processing device 26 will co-operate with the systems 3, 4, 5, 6 and 12 described above so as to assist, step by step, the operator in the manual preparation of the liquid pharmaceutical composition.

Figure 2:
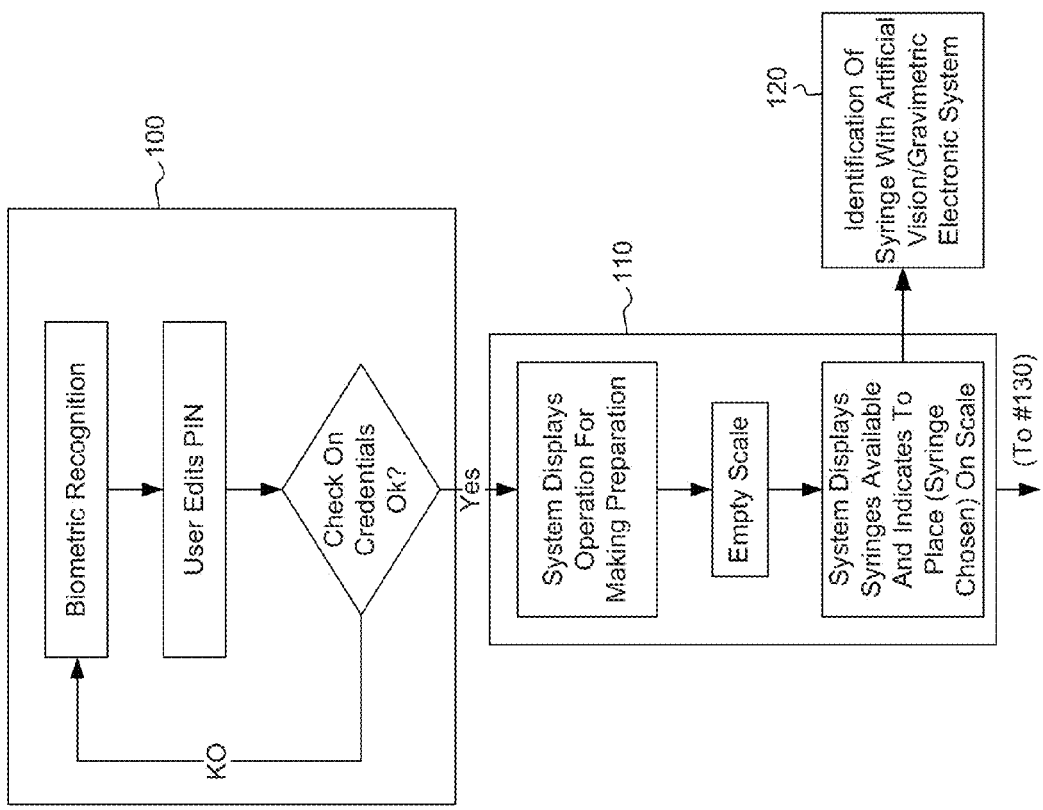
FIG. 2 is a flowchart of the operation of the digital assistance equipment illustrated in FIG. 1; whilst
Figure 2:
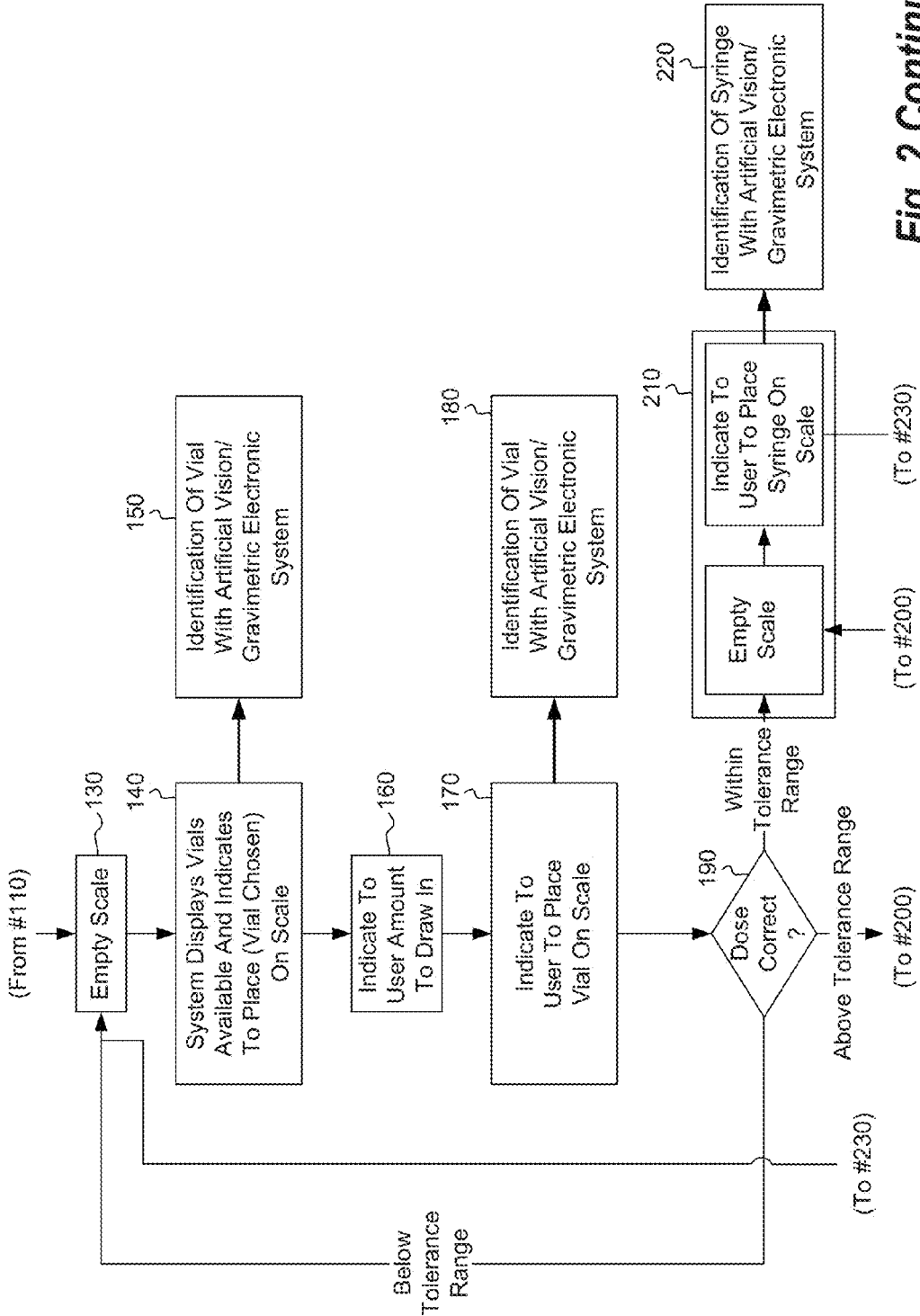
Figure 2:
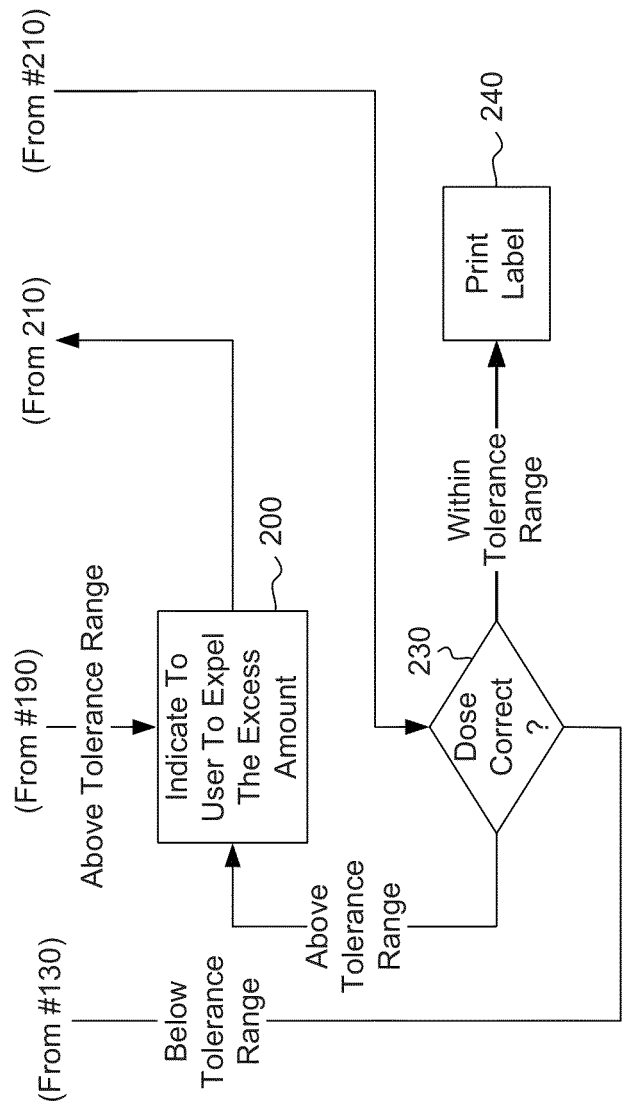
Figure 3:
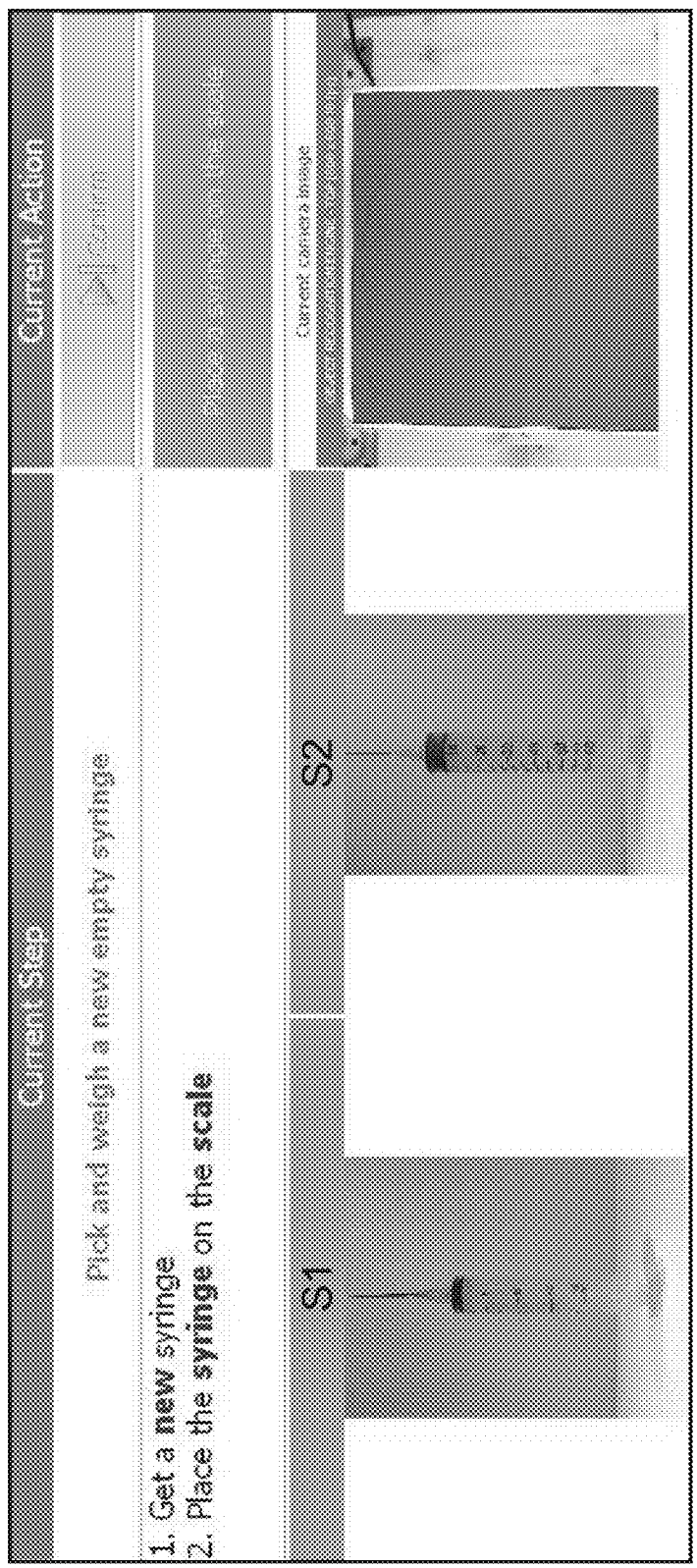

The flowchart of FIG. 2 shows the operations of the operating method implemented by the processing system 6 of the equipment 1, whilst FIGS. 3-10 show a possible example of the graphic interfaces generated by the digital assistant appliance 1.

In particular, described in what follows are the operations implemented by the digital assistant appliance 1 for the preparation of a liquid pharmaceutical composition provided by way of example in which, for simplicity of description, but without this implying any loss in generality, the use of a single-dose PA of an active principle contained in two different types of vials designated by F1 and F2 is envisaged, and in which transfer of the active principle envisaged by the pharmaceutical preparation according to the example can be performed through two different types of syringes S1 and S2.

It should however be noted that the operations described in what follows can be implemented by the method, in a way altogether similar, also in the case where the liquid pharmaceutical composition envisages a plurality of active principles and/or doses.

The method envisages authorizing an operator to access the digital assistance appliance 1 only following upon an authentication step.

In particular, the authentication step comprises an operator image recognition, for example the face or parts of the face, for example the eyes, acquired via the videocamera 12, and/or verification of the data identifying the operator contained in the smartcard and/or in the transponder 36 entered by the operator himself through the user-interface system 5 (block 100).

Once the authentication step is through, the processing system determines the medical prescription of the liquid pharmaceutical composition to be prepared.

In particular, the processing system 6 determines the medical prescription on the basis of a direct selection of the prescription and/or of the patient carried out by the operator through the user-interface system 5 and/or on the basis of the reading of a barcode performed using the barcode-reader device 23.

It should be noted that the barcode could be present on a sheet of paper and contain data that identify the medical prescription and/or the information necessary for preparation of the liquid pharmaceutical composition, i.e., the active principles, the dose of each active principle, as well as the types of syringes and the types of vials that can be used in the preparation.

According to a different embodiment the processing system 6 can determine the medical prescription, through the transponder-reader apparatus 37, on the basis of a reading of a transponder 39 containing the aforesaid data regarding the medical prescription itself.

The processing system 6 is moreover configured to enable the operator to establish, through the user-interface system 5, the use of a spike coupled directly to the syringe or of a spike coupled directly to the vial in the step of preparation of the liquid pharmaceutical composition.

The method comprises the step of determining: the different types of syringes that can be used in the preparation, which in the example illustrated are designated by S1 and S2 and, at the same time, the different types of vials that can be used in the preparation itself, which in the example illustrated are designated by F1 and F2, on the basis of the medical prescription and data contained in the memory device 15.

The method implemented by the processing system 6 comprises the step of communicating to the operator a preparation assisting message which indicates to the operator to select one of the different types of possible syringes and to position the syringe selected on the scale 8 (block 110).

In particular, the method can generate a graphic interface through the user-interface system 5 (illustrated, for example, in FIG. 3), wherein the types of syringes S1 and S2 and the first message for assistance to preparation are displayed.

The method implemented by the processing system 6 moreover comprises preferably, but not necessarily, a step in which it receives the selection regarding the use of a spike coupled to the vial or to the syringe by the operator.

For this purpose, the graphic interface can be configured for displaying a selection window (not illustrated), through which the operator can establish the use of the spike-syringe or spike-vial configuration.

The method implemented by the processing system 6 comprises the step of activating a procedure of visual identification of the syringe positioned on the scale 8, through the artificial viewing system 4, to verify whether the syringe identified corresponds or not to one of the types of syringes S1 or S2 that can be selected.

Figure 4:
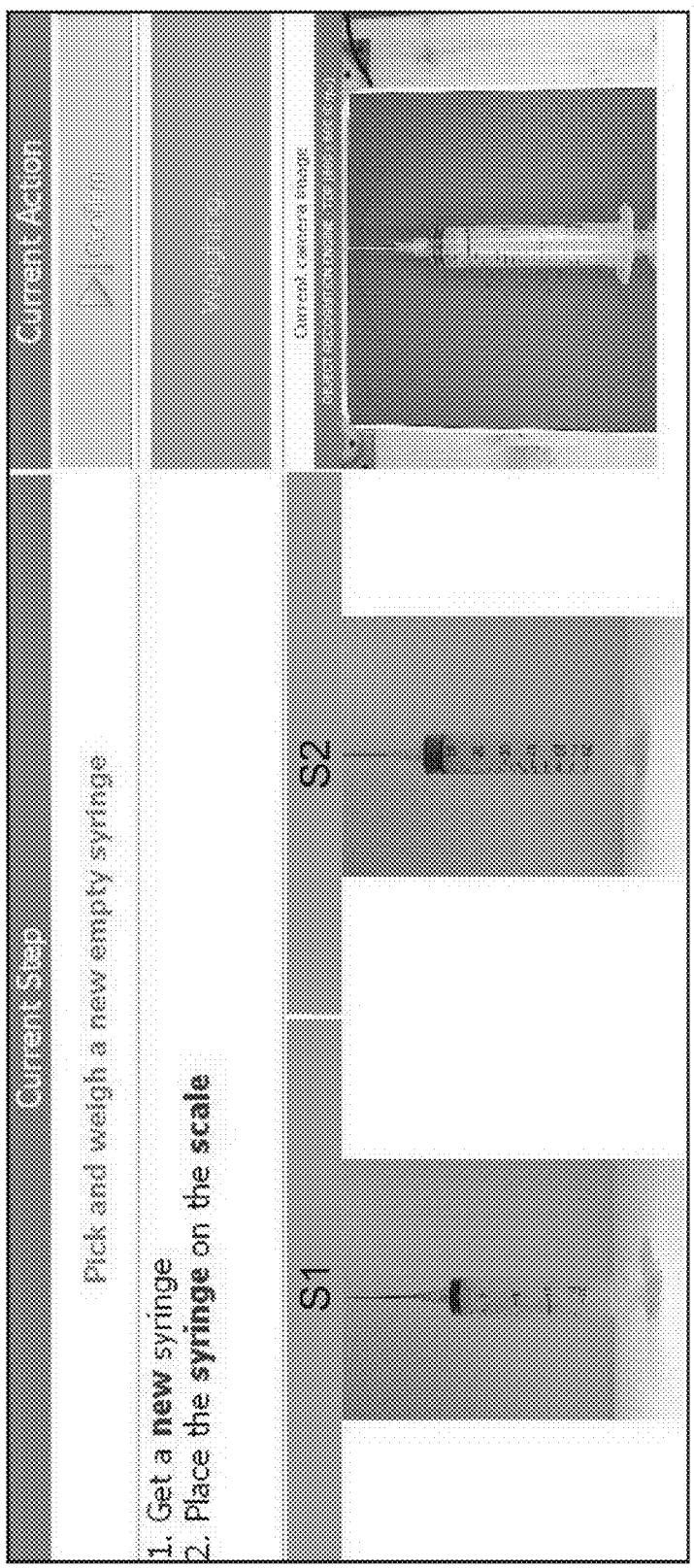
Figure 5:
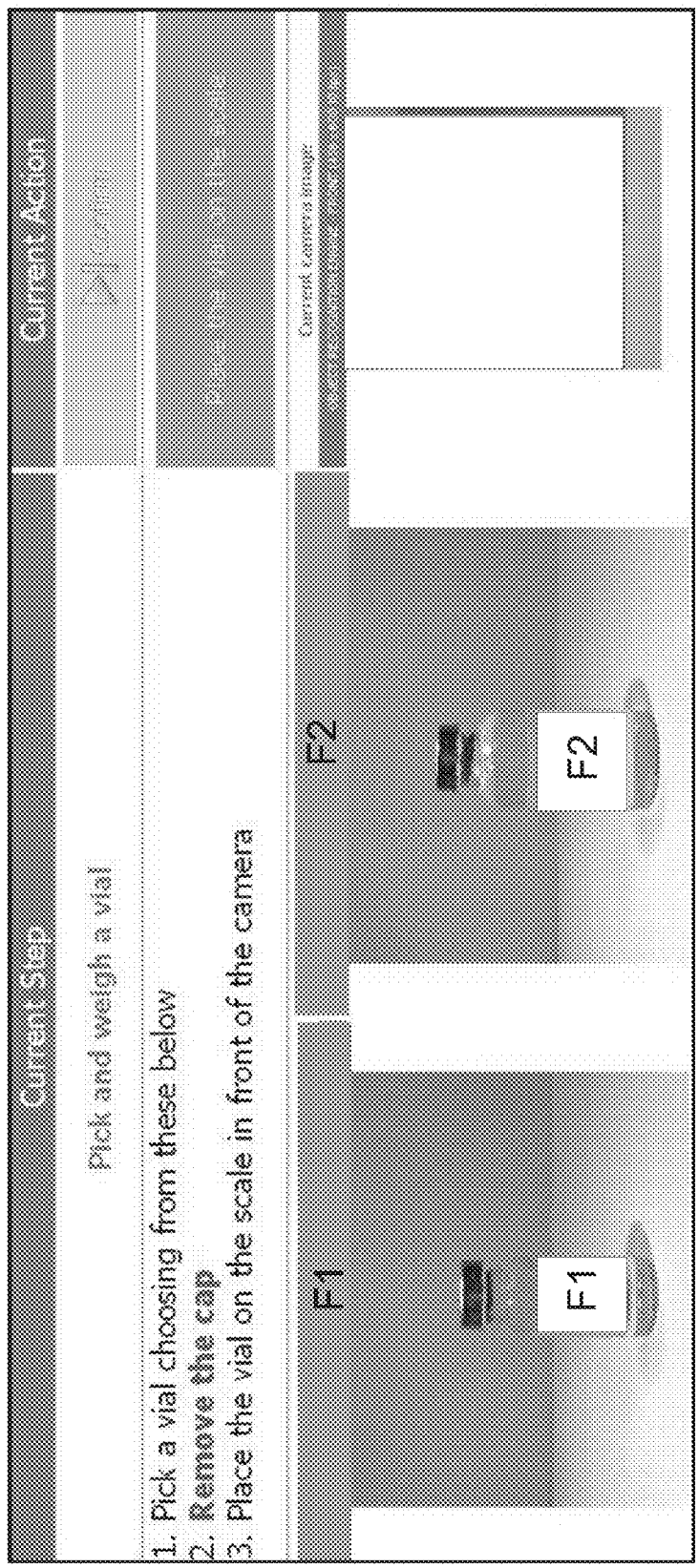
Figure 6:
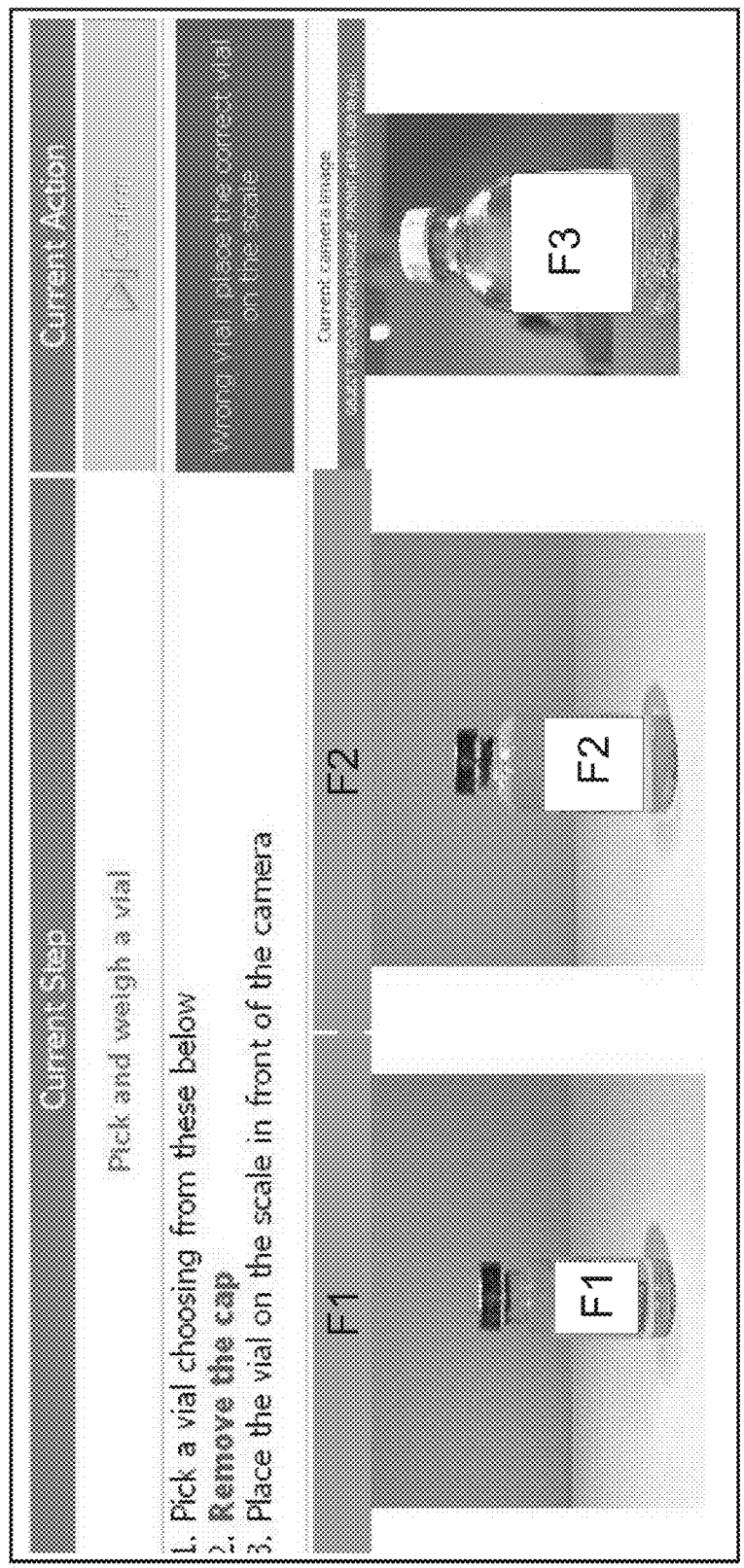
Figure 7:
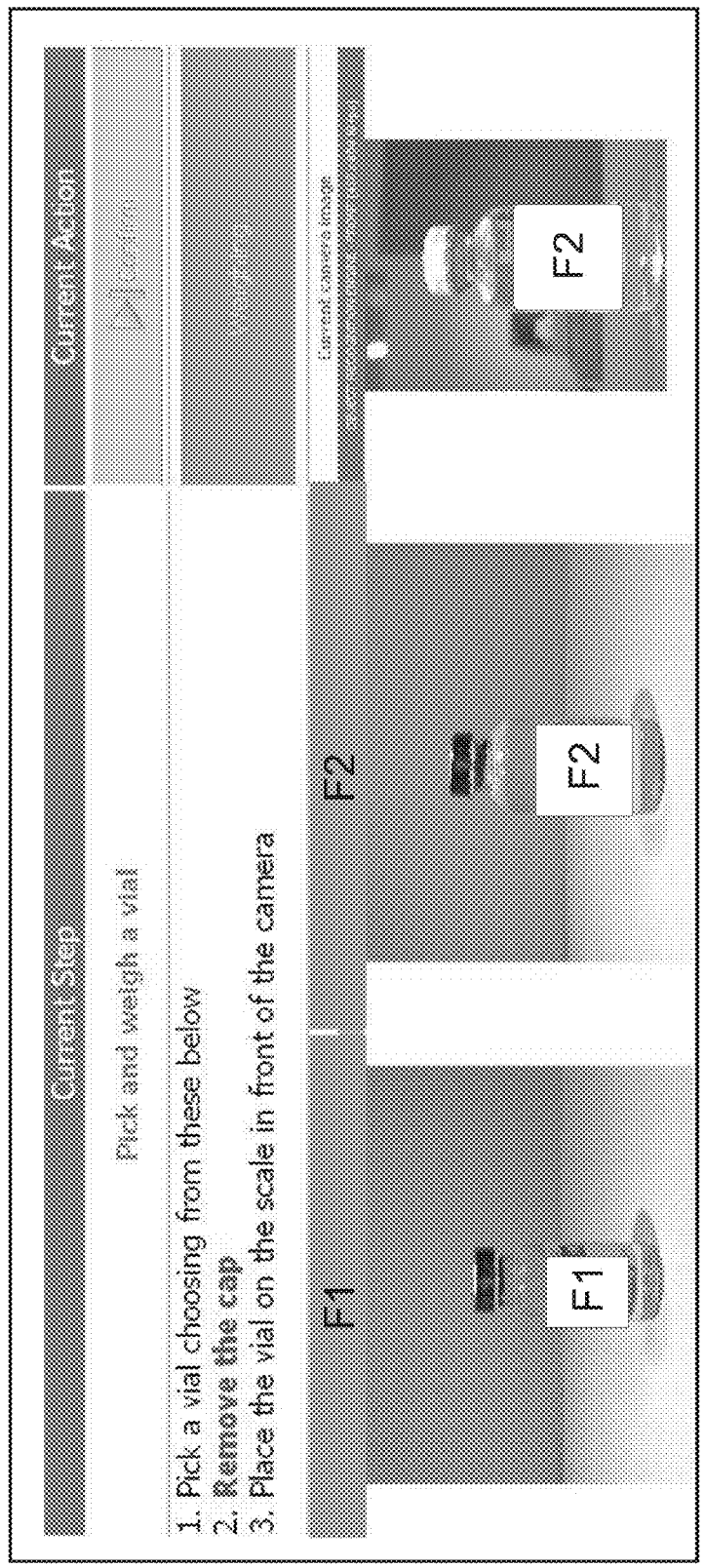
Figure 8:

In this step, the artificial viewing system 4 identifies the syringe by comparing the image of the syringe acquired by the top videocamera 9 and/or the front videocamera 10, with the syringe sample images associated to the types of syringe S1 and S2 (block 120) (example illustrated in FIG. 4).

The comparison of the images can be made by the processing system 6 via a pattern-matching algorithm.

On the basis of the outcome of said comparison, the processing system 6 can determine: a) the presence of a correct syringe, i.e., corresponding to one of the two types proposed; or b) the presence of an incorrect syringe, i.e., not corresponding to either of the two types proposed; or c) the presence of a correct syringe having a configuration different from the preset one, i.e., without needle, or provided with a protective cap for the needle.

In the case where in the starting step, the operator has selected the spike-syringe combination, and/or the syringe is incorrect—condition b)—the method implemented by the processing system 6 can determine, on the basis of the comparison between the image acquired and the syringe-spike sample image associated to the type of syringe identified, whether k) the spike has been coupled to the syringe or z) the syringe is without a spike.

If the processing system 6 determines the conditions a) or k), it detects correctness of the operations carried out by the operator.

If the processing system 6 determines the condition b), then it communicates to the operator a message of error of selection of the syringe, where it is required to remove the syringe from the scale 8 and to repeat the weighing operation with one of the syringes belonging to types S1 or S2.

If the processing system 6 determines the condition c), then it communicates to the operator an additional message in which it requires coupling of the needle to the syringe selected or removal of the protective cap for the needle from the syringe.

If the processing system 6 determines the condition z), then it communicates to the operator an additional message in which it requires coupling of the spike to the syringe.

The operator removes the syringe from the scale 8, and: in the condition b) replaces the syringe with a new syringe, and positions the latter on the scale 8; in the condition c) the operator couples the needle to the syringe or removes the protective cap from the needle, and places the syringe again on the scale 8; whereas in the condition z) the operator couples the spike to the syringe and again places the latter on the scale 8. At this point, the processing system 6 once again repeats the operations of identification of the syringe described above (block 120).

If condition a) or condition k) arises, and assuming selection of the syringe S2 by the operator, the processing system 6 measures the weight of the syringe P=PS2$a$, through the gravimetric control system 4 and calculates the final weight PS2$a$+PA that the syringe S2 will have to have once the active principle has been drawn into the syringe, where PA is the weight of the preset dose of the active principle prescribed in the medical prescription (block 120).

The processing system 6 communicates to the operator a preparation assisting message which requires removal of the syringe S2 from the scale 8 (block 130).

The processing system 6 communicates to the operator a preparation assisting message indicating to select one of the different types of vials possible F1 or F2 and to position the vial selected on the scale 8 (block 140).

In particular, the processing system 6 can generate a graphic interface through the user-interface system 5 (illustrated in FIG. 5), where the two types of vial F1 and F2 and the preparation assisting message are displayed.

The program implements a procedure of visual identification of the vial positioned on the scale 8, through the artificial viewing system 4, and verifies whether the vial identified corresponds or not to one of the types of vials that can be selected F1 and F2.

In this step, the artificial viewing system 4 identifies the vial by comparing the image of the vial acquired by the top videocamera 9 and/or by the front videocamera 10 with the vial sample images associated to the two types of vial available F1 and F2 (block 150).

On the basis of said comparison, which can be carried out via a pattern-matching algorithm, the processing system 6 determines: e) the presence of a correct vial, i.e., corresponding to one of the two types proposed F1 or F2; or f) the presence of an incorrect vial, i.e., different from the two types proposed; or g) the presence of a correct vial having a configuration different from the preset one (for example, with a lid).

In the case where, in the starting step, the operator has selected the spike-vial coupling, and/or the vial is correct—condition e)—the method implemented by the processing system 6 can determine, on the basis of the comparison between the image acquired and the vial-spike sample image associated to the type of vial identified either x) that the spike has been coupled to the vial or y) that the vial is without a spike.

If the processing system 6 determines the condition f) (example illustrated in FIG. 6, where a vial F3 different from F1 or F2 has been selected), then it communicates to the operator a message in which it is required to remove the vial F3 from the scale 8, to select a vial belonging to one of the two types displayed F1 or F2, and to place the new vial selected on the scale 8. In the condition g), the processing system 6 communicates to the operator a message in which it requires removal of the lid from the vial, whereas in the condition y) it communicates to the operator a message in which it requires coupling of the spike to the vial.

The operator removes the incorrect vial from the scale 8, and, in the case f), positions the new vial on the scale 8; in the case g) the operator arranges the vial without lid on the scale 8; whereas in the case y) the operator couples the spike to the vial and again positions the vial on the scale 8.

At this point, the processing system 6 once again repeats the operations of recognition of the vial described above.

Where the case e) (FIG. 7) or the case x) (not illustrated) arises, the processing system 6 measures and stores, through the gravimetric control system 4, the weight PF2$a$ of the vial F2 (or of the vial-spike) selected.

The processing system 6 communicates to the operator a preparation assisting message that indicates to remove the vial F2 from the scale 8 and draw from the vial F2 itself, using the syringe S2, a dose PA of active principle (block 160). In particular, the aforesaid preparation assisting message of assistance can be communicated to the operator by the processing system 6 through a graphic interface illustrated in the example of FIG. 8.

Figure 9:
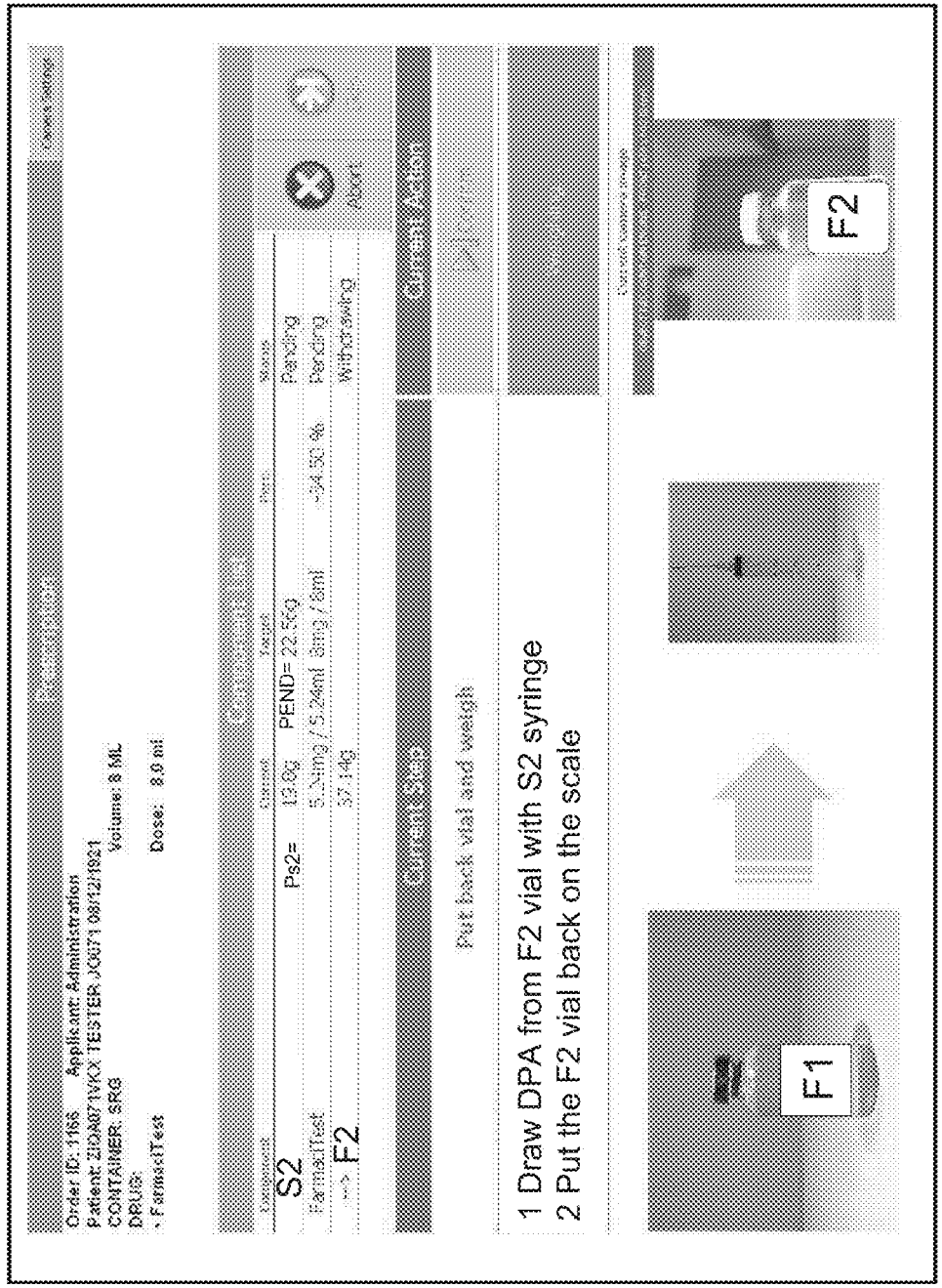

The processing system 6 again communicates to the operator a message for assistance to preparation which requires him to place the vial F2 on the scale 8 (block 170) (graphic interface illustrated in FIG. 9).

The processing system 6 again carries out the procedure of visual identification of the vial F2 present on the scale (block 180) executing again the operations of block 150.

If the vial identified does not correspond to the vial F2 (or to the vial coupled to the spike) recognized in the course of the previous identification procedure, the processing system communicates to the operator an error condition of the vial and remains in a condition of waiting to receive the correct vial (and/or the vial coupled to the spike in the case of selection of vial-spike configuration).

If, instead, the vial identified does correspond to the vial F2 recognized in the previous step, then the processing system measures the weight PF2$b$ of the vial F2, calculates the difference DPF=PF2$a$-PF2$b$ between the weight PF2$b$ of the vial F2 measured subsequently to aspiration of the active principle and the weight PF2$a$ of the vial F1 measured prior to aspiration.

The program verifies whether the difference of weight DPF of the vial corresponds to the weight PA of the active principle prescribed in the medical prescription (block 190).

In the case where the difference of weight DPF is less than a preset minimum threshold SPTOLmin that sets the lower limit of a tolerance range DPTOL, the processing system 6 communicates to the operator a message for assistance to preparation indicating an underdosing of the active principle and at the same time the need to transfer from the vial F2 to the syringe S2 an additional quantity DAGG of active principle having a weight equal to DAGG=PA−DPF.

In this case, the program again executes the operations described in blocks 130-180.

If, instead, the difference of weight DPF is above the preset maximum threshold SPTOLmax, the program communicates to the operator a message for assistance to preparation indicating an overdosing of the active principle and at the same time the need to expel from the syringe a quantity DESP of active principle having a weight equal to DESP=DPF−PA (block 200).

If, instead, the difference of weight DPF is within the tolerance range DPTOL, the processing system 6 communicates to the operator an assistance preparation message indicating the need to remove the vial F2 from the scale 8 and to position on the latter the syringe for a new weighing operation (block 210).

The processing system 6 again carries out the procedure of visual identification of the syringe present on the scale 8 (block 220), implementing the same operations described in block 120.

If the recognition of the syringe has a negative outcome, the processing system 6 warns the operator that an incorrect syringe has been placed on the scale 8 and remains waiting for repositioning of the correct syringe on the scale 8.

If, instead, the recognition of the syringe has a positive outcome, then the processing system 6 measures the weight PS2b of the syringe S2, calculates the difference DPS=PS2b−PSa between the weight PS2b of the syringe S2 measured subsequently to drawing-in of the active principle and the weight PS2a thereof measured prior to drawing-in (block 230).

In the case where the difference in weight DPS is less than the preset minimum threshold SPTOLmin, the processing system 6 communicates to the operator a assistance preparation message indicating a condition of underdosing of active principle in the syringe S2 and the need to transfer from the vial, F2 and F1 in the example, to the syringe S2 an additional amount of active principle having a weight equal to DAGG=PA−DPS. In this case, the program again executes the operations described in blocks 130-210.

If instead the weight difference DPS is greater than the preset maximum threshold SPTOLmax that sets an upper limit of the tolerance range DPTOL, the processing system 6 communicates to the operator a message for assistance to preparation indicating the condition of overdosing of active principle in the syringe S2 and the need to expel from the syringe S2 an amount DESP of active principle having a weight equal to DESP=DPS−PA (block 200). At this point, the processing system 6 communicates to the operator an assistance preparation message indicating the need to weigh again the syringe and once again repeats the operations of blocks 210, 220, 230.

If, instead, the difference in weight DPS is within the tolerance range DPTOL, the processing system 6 communicates to the operator a message indicating the end of the preparation and preferably, but not necessarily, prints, via the printing device 24, a label that contains the data regarding the liquid pharmaceutical composition and can be affixed to the medical instrument 2.

The liquid pharmaceutical composition present in the syringe can be transferred by the operator from the syringe itself to the medical instrument 2 for administering the liquid pharmaceutical composition to the patient, which can correspond to an infusion sac or to an elastomeric pump. It should be noted that in the case where the liquid pharmaceutical composition comprises a single active principle (as in the example described above) the medical instrument 2 can correspond to the syringe used for drawing in the active principle from the vial during preparation.

The digital assisting appliance described above presents the major advantage of providing assistance to the operator that is able to increase assurance of correctness of the manual preparation of the liquid pharmaceutical composition as compared to the assistance provided by known assistance equipment.

In fact, the digital assistance appliance described above is able to ensure timely recognition of error conditions in the weighing operation, whenever there occur, in the course of the preparation, accidental modifications of the configuration of the syringe or of the vial.

In the second place, the digital assistant appliance, thanks to the artificial visual verification on the vial and on the syringe, markedly reduces the risk of using incorrect active principles.

Finally, the digital assistant appliance conveniently enables the operator to choose different types of syringes and/or vials for preparation of a given liquid pharmaceutical composition, at the same time guaranteeing a high degree of safety.

Finally, it is clear that modifications and variations may be made to the digital assistant appliance and to the method described and illustrated above, without thereby departing from the scope of the present invention.

The invention claimed is:

1. A digital assistant appliance configured to assist and to monitor an operator as the operator manually prepares a liquid pharmaceutical composition to be administered to a patient using a medical instrument, said appliance comprising:
   a user-interface system configured to indicate, to the operator, operations to be performed by the operator to prepare the liquid pharmaceutical composition and to provide assistance preparation messages to the operator as the operator prepares the liquid pharmaceutical composition;
   a memory device configured to have stored thereon, for each active principle of the liquid pharmaceutical composition: one or more first sample images of vials that can contain said active principle, and/or one or more second sample images of syringes that can be used to transfer said active principle from the vials to the medical instrument;
   a scale positioned on a horizontal surface, the scale being configured to have positioned thereon, by the operator, a vial and/or a syringe;
   an artificial viewing system configured to acquire: a vial image of the vial positioned by the operator on said scale and/or a syringe image of the syringe positioned by the operator on said scale; and
   an electronic processing system configured to:
   compare said acquired vial image with each of said first sample images and determine that an incorrect vial has been positioned on said scale by the operator, when said acquired vial image does not correspond to any of said first sample images;
compare the acquired syringe image with each of said second sample images and determine that an incorrect syringe has been positioned on said scale by the operator, when said acquired syringe image does not correspond to any of said second sample images; and
provide a warning to the operator, through the user-interface system, when the electronic processing system determines that an incorrect vial and/or an incorrect syringe has been positioned on said scale by the operator.

2. The appliance according to claim 1, wherein said electronic processing system is further configured to:
compare said acquired vial image with each of said first sample images to determine whether the vial positioned on said scale has at least one additional component with respect to a preset main configuration envisaged in the manual preparation of the liquid pharmaceutical composition; and
provide a warning to the operator, through the user-interface system, when the electronic processing system determines the presence of said additional component.

3. The appliance according to claim 1, wherein said electronic processing system is further configured to:
compare said acquired syringe image with each of said second sample images to determine whether the syringe positioned on said scale is without preset components and/or has additional components with respect to a preset basic configuration envisaged in the manual preparation of the liquid pharmaceutical composition; and
provide a warning to the operator, through the user-interface system, when the electronic processing system determines the absence of the preset components and/or the presence of additional components.

4. The appliance according to claim 1, wherein:
said memory device is configured to have stored thereon, for each active principle of the liquid pharmaceutical composition, a corresponding preset weight;
said scale comprises:
a gravimetric control system for weighing said vial and/or said syringe positioned on said scale; and
said electronic processing system is further configured to:
calculate the weight of the active principle contained in said syringe on the basis of a weighing of said syringe or of said vial before and after a step of drawing, by the operator, the active principle from said vial;
compare the calculated weight of the active principle contained in said syringe with the preset weight for determining whether a dose of the active principle contained in the syringe is incorrect; and
provide a warning to the operator, through the user-interface system, when the electronic processing system determines that an incorrect weight of said active principle is contained in said syringe.

5. The appliance according to claim 1, wherein:
said memory device is configured to have stored thereon, for each type of syringe, a syringe-spike sample image corresponding to a configuration of a syringe coupled to a spike and/or, for each vial, a vial-spike sample image corresponding to a configuration of coupling of said vial to a spike;
said electronic processing system is further configured to:
receive, through the user-interface system, a user-selection command indicating the syringe-spike coupling and/or the vial-spike coupling;
compare the acquired vial image with said vial-spike sample image and/or the acquired syringe image with said syringe-spike sample image, based on the user-selection command, to determine the absence of the spike when said acquired vial image and/or said acquired syringe image do not correspond to said vial-spike sample image and/or syringe-spike sample image; and
provide a warning to the operator, through the user-interface system, when the electronic processing system determines the absence of the spike.

6. The appliance according to claim 1, wherein the warning provided by the electronic processing system to the operator comprises directing the operator, through the user-interface system, to manually replace the vial and/or the syringe on said scale.

7. A method of assisting and monitoring an operator as the operator manually prepares a liquid pharmaceutical composition to be administered to a patient using a medical instrument, the method being performed by a digital assistant appliance and comprising:
storing in a memory device, for each active principle of the liquid pharmaceutical composition, one or more first sample images of vials that can contain said active principle, and/or one or more second sample images of syringes that can be used to transfer the active principle from said vials to the medical instrument;
acquiring, through an artificial viewing system, a vial image of a vial positioned on a scale by the operator and/or a syringe image of a syringe positioned on said scale by the operator;
comparing said acquired vial image with each of said first sample images to determine whether the vial positioned on said scale by the operator is incorrect; and/or
comparing said acquired syringe image with each of said second sample images to determine whether the syringe positioned on said scale by the operator is incorrect; and
providing a warning to the operator, through a user-interface system, when the vial positioned on said scale is incorrect and/or the syringe positioned on said scale is incorrect.

8. The method according to claim 7, further comprising:
comparing said acquired vial image with each of said first sample images to determine whether the vial positioned on said scale has at least one additional component with respect to a preset main configuration; and
providing a warning to the operator, through the user-interface system, when said vial is determined to have said additional component.

9. The method according to claim 7, further comprising:
comparing said acquired syringe image with each of said second sample images to determine whether the syringe positioned on said scale is without preset components and/or has additional components with respect to a preset basic configuration; and
providing a warning to the operator, through the user-interface system, when said syringe is determined to be without the preset components or to have additional components.

10. The method according to claim 7, further comprising:
storing in said memory device, for each active principle of the liquid pharmaceutical composition, a corresponding preset weight;
weighing said vial or said syringe a first time via a gravimetric control system provided with said scale;
weighing said vial or said syringe a second time via the gravimetric control system, the first and second weighings being respectively performed before and after the active principle has been manually drawn from said vial by the operator using said syringe;

calculating the weight of the active principle contained in said syringe on the basis of the first and second weighings;

comparing the calculated weight of the active principle contained in said syringe with the preset weight to determine whether a dose of the active principle contained in the syringe is incorrect; and providing a warning to the operator, through the user-interface system, when an incorrect weight of said active principle contained in said syringe is determined.

11. The method according to claim 7, further comprising:
storing in said memory device, for each type of syringe, a syringe-spike sample image corresponding to a configuration of a syringe coupled to a spike and/or, for each vial, a vial-spike sample image corresponding to a configuration of coupling of said vial to a spike;

receiving, through the user-interface system, a user-selection command indicating the syringe-spike coupling and/or the vial-spike coupling;

comparing the acquired vial image with said vial-spike sample image and/or the acquired syringe image with said syringe-spike sample image, based on the user-selection command, to determine the absence of the spike when said acquired vial image and/or said acquired syringe image do not correspond to said vial-spike sample image and/or syringe-spike sample image; and providing a warning to the operator, through the user-interface system, when the absence of the spike is determined.

12. The method according to claim 7, further comprising:
directing the operator, through the user-interface system, to set the vial and/or the syringe on the scale, the step of directing the operator being performed before the step of acquiring a vial image and/or a syringe image.

13. The method according to claim 7, wherein providing a warning to the operator comprises directing the operator, through the user-interface system, to manually replace the vial and/or the syringe on said scale.

14. A non-transitory computer readable medium having stored thereon instructions that, when executed by a computing device, cause to be performed a method of assisting and monitoring an operator as the operator manually prepares a liquid pharmaceutical composition to be administered to a patient using a medical instrument, the method being performed by a digital assistant appliance and comprising:
storing in a memory device, for each active principle of the liquid pharmaceutical composition, one or more first sample images of vials that can contain said active principle, and/or one or more second sample images of syringes that can be used for transferring to transfer the active principle from said vials to the medical instrument;

acquiring, through an artificial viewing system, an image of a vial positioned on a scale of the appliance by the operator and/or an image of a syringe positioned on the scale by the operator;

comparing said acquired vial image with each of said first sample images to determine whether the vial positioned on the scale by the operator is incorrect; and/or comparing said acquired syringe image with each of said second sample images to determine whether the syringe positioned on the scale by the operator is incorrect; and providing a warning to the operator, through a user-interface system, when the vial positioned on said scale is incorrect and/or the syringe positioned on said scale is incorrect.

15. The non-transitory memory device according to claim 14, wherein the medium has stored thereon further instructions that, when executed by the computing device, causes to be performed:
directing the operator, through the user-interface system, to set the vial and/or the syringe on the scale, the step of directing the operator being performed before the step of acquiring a vial image and/or a syringe image.

16. A method of preparing a liquid pharmaceutical composition to be administered to a patient using a medical instrument, the liquid pharmaceutical composition comprising one or more active principles, the method comprising:
for each active principle:
manually positioning, by an operator, a vial and a syringe to be imaged;

acquiring, by a digital assistant appliance, images of the manually positioned vial and syringe;

comparing, by the digital assistant appliance, the acquired images of the vial and the syringe with images of sample vials that can contain the active principle and images of sample syringes that can be used to transfer the active principle from the sample vials to the medical instrument, to determine if the manually positioned vial and syringe respectively correspond to one of the sample vials and one of the sample syringes;

if it is determined that the manually positioned vial and syringe respectively correspond to one of the sample vials and one of the sample syringes, drawing, by the operator, the active principle from the vial using the syringe to transfer to the medical instrument; and if it is determined that the manually positioned vial and/or syringe do not respectively correspond to any of the sample vials or sample syringes, providing a warning to the operator, by the digital assistant appliance.

17. The method recited in claim 16, wherein providing a warning to the operator comprises directing the operator, by the digital assistant appliance, to manually replace the vial and/or syringe.

18. The method recited in claim 16, further comprising:
weighing, by the digital assistant appliance, the vial or the syringe a first time, before the step of manually using the syringe to draw the active principle from the vial;

weighing, by the digital assistant appliance, the vial or the syringe a second time, subsequent to the step of manually using the syringe to draw the active principle from the vial;

calculating, by the digital assistant appliance, the weight of the active principle contained in the syringe on the basis of the first and second weighings;

comparing, by the digital assistant appliance, the calculated weight of the active principle contained in the syringe with preset dosing weights corresponding to the active principle to determine if the calculated weight corresponds to a preset dosing weight corresponding to the active principle;

if it is determined that the calculated weight corresponds to the preset dosing weight, transferring, by the operator, the active principle from the syringe to the medical instrument; and if it is determined that the calculated weight does not correspond to the preset dosing weight, providing a warning to the operator, by the digital assistant appliance.

\* \* \* \* \*